(12) United States Patent
Miwa et al.

(10) Patent No.: US 10,182,721 B2
(45) Date of Patent: Jan. 22, 2019

(54) FUNDUS IMAGING APPARATUS

(71) Applicant: TOPCON CORPORATION, Itabashi-ku (JP)

(72) Inventors: Akemi Miwa, Kawaguchi (JP); Tatsuo Yamaguchi, Warabi (JP); Makoto Saika, Nerima-ku (JP)

(73) Assignee: TOPCON CORPORATION, Itabushi-ku (JP)

( * ) Notice: Subject to any disclaimer, the term of this patent is extended or adjusted under 35 U.S.C. 154(b) by 0 days.

(21) Appl. No.: 15/202,963

(22) Filed: Jul. 6, 2016

(65) Prior Publication Data

US 2017/0055831 A1 Mar. 2, 2017

(30) Foreign Application Priority Data

Aug. 25, 2015 (JP) .................... 2015-165991

(51) Int. Cl.
*A61B 3/14* (2006.01)
*A61B 3/12* (2006.01)
(Continued)

(52) U.S. Cl.
CPC .............. *A61B 3/14* (2013.01); *A61B 3/1015* (2013.01); *A61B 3/1025* (2013.01); *A61B 3/12* (2013.01);
(Continued)

(58) Field of Classification Search
CPC ....... A61B 3/14; A61B 3/0025; A61B 3/1025; A61B 3/12; A61B 3/1225; G02B 6/06; G02B 21/0056; G02B 26/103
(Continued)

(56) References Cited

U.S. PATENT DOCUMENTS

2002/0139920 A1  10/2002  Seibel et al.
2012/0044457 A1  2/2012  Sato et al.
(Continued)

FOREIGN PATENT DOCUMENTS

KR  10-2012-0101040 A  9/2012
WO  WO 2010/134641 A1  11/2010

OTHER PUBLICATIONS

Extended European Search Report dated Feb. 2, 2017 in Patent Application No. 16179646.1.
(Continued)

*Primary Examiner* — Bumsuk Won
*Assistant Examiner* — Wen Huang
(74) *Attorney, Agent, or Firm* — Oblon, McClelland, Maier & Neustadt, L.L.P.

(57) ABSTRACT

According to one embodiment, a fundus imaging apparatus includes a light source, an optical scanner, an optical fiber, a light guide system, a photodetector unit, and an image forming unit. The optical scanner scans the fundus of a subject's eye with light from the light source. The optical fiber includes a plurality of optical waveguides. The light guide system guides the light returning from the fundus to the entrance end of the optical fiber. The photodetector unit detects light output from each of at least three regions at the exit end of the optical fiber. The image forming unit forms a first image based on a detection result of light output from a first region of the at least three regions, and a second image based on detection results of light output from two or more regions of the at least three regions other than the first region.

7 Claims, 10 Drawing Sheets

(51) Int. Cl.
 A61B 3/10 (2006.01)
 G02B 6/06 (2006.01)
 G02B 21/00 (2006.01)
(52) U.S. Cl.
 CPC .............. *A61B 3/1225* (2013.01); *G02B 6/06* (2013.01); *G02B 21/0028* (2013.01); *G02B 21/0056* (2013.01); *G02B 21/0064* (2013.01)
(58) Field of Classification Search
 USPC ........................................................ 351/206
 See application file for complete search history.

(56) References Cited

U.S. PATENT DOCUMENTS

2012/0226150 A1 9/2012 Balicki et al.
2015/0173604 A1 6/2015 Wheatley

OTHER PUBLICATIONS

T. Wilson et al. "Differential Amplitude Contrast Imaging in the Scanning Optical Microscope", Applied Physics B 32, 1983, 5 pages.
Yusufu N. Sulai et al "Visualization of retinal vascular structure and perfusion with a nonconfocal adaptive optics scanning light ophthalmoscope", J. Opt. Soc. Am. A., vol. 31, No. 3, 2014, 11 pages.
Drew Scoles et al "In Vivo Imaging of Human Cone Photoreceptor Inner Segments", Investigative Ophthalmology & Visual Science (IOVS), vol. 55, No. 7, 2014, 8 pages.
Ethan A. Rossi et al "Adaptive Optics Imaging of Putative Cone Inner Segments Within Geographic Atrophy Lesions", ARVO 2015, 1 page.

FUNDUS IMAGING APPARATUS

CROSS-REFERENCE TO RELATED APPLICATION

This application is based upon and claims the benefit of priority from Japanese Patent Application No. 2015-165991, filed 25 Aug. 2015; the entire contents of which are incorporated herein by reference.

FIELD

Embodiments described herein relate generally to a fundus imaging apparatus.

BACKGROUND

Contour enhanced images can be acquired by a scanning microscope using split detection (see, for example, T. Wilson and D. K. Hamilton, "Differential amplitude contrast imaging in the scanning optical microscope", Applied Physics, B. 1983, pp. 187-191). In recent years, studies have been made to observe the morphology of the fundus in more detail by applying this technique to the scanning laser ophthalmoscopy (SLO) (see, for example, Yusufu N. Sulai, Drew Scoles, Zachary Harvey, and Alfredo Dubra, "Visualization of retinal vascular structure and perfusion with a nonconfocal adaptive optics scanning light ophthalmoscope", J. Opt. Soc. Am. A 2014 pp. 569-579; Drew Scoles, Yusufu N. Sulai, Christopher S. Langlo, Gerald A. Fishman, Christine A. Curcio, Joseph Carroll, and Alfredo Dubra, "In vivo imaging of human cone photoreceptor inner segments", IOVS. 14-14542, pp. 4244-4251; Ethan A Rossi, Kenichi Saito, Charles E. Granger, Koji Nozato, Qiang Yang, Tomoaki Kawakami, Jie Zhang, William Fischer, David R Williams, and Mina M Chung, "Adaptive optics imaging of putative cone inner segments within geographic atrophy lesions", ARVO 2015).

The split detection method uses a peripheral light beam around the point image center area in the fundus conjugate point. The peripheral light beam is divided into a plurality of light beams. The arithmetic processing is performed by using the light beams to thereby obtain a phase contrast image of a different frequency band from that of a fundus conjugate point image. Such a split detection method is expected as a technology that allows the observation of the fundus tissues (especially, inner segment of photoreceptor cells) with no successful in vivo visualization heretofore.

In the conventional configuration, first, a light beam is separated into a light beam of the point image center area and a peripheral light beam around it by a light beam splitting element (e.g., annular mirror having an annular opening, etc.) arranged in a fundus conjugate point. The peripheral light beam is divided into a plurality of light beams by a light beam splitting element (e.g., edge mirror, etc.) arranged in a fundus conjugate point newly formed by an imaging optical system. Each of the light beams is received by a detector.

The light beam is required to be separated into the light beam of the point image center area and the peripheral light beam with high accuracy in the fundus conjugate point. However, since the point image size (Airy disk diameter) in the fundus conjugate point is several 10 μm to several 100 μm, a very high degree of accuracy is required to manufacture and install the light beam splitting element. As well as increasing the cost, it also increases the time required for alignment work.

In addition, with the use of the above-mentioned light beam splitting element, it is very difficult to change the number of divisions of the peripheral light beam. For example, to increase the number of divisions, it is necessary to newly form a fundus conjugate point. As a result, the long optical system and detectors provided as many as the number of divisions make it difficult to ensure the installation space. On the contrary, in some cases, the number of divisions is limited in relation to the installation space.

Further, in the conventional configuration, it is very difficult to change the division pattern, such as dividing direction of the peripheral light beam. For example, to change the dividing direction, highly accurate alignment work is newly required.

SUMMARY

Embodiments are intended to solve the above problems, and one object thereof is to provide a novel technology for the fundus imaging apparatus that uses split detection.

According to one embodiment, a fundus imaging apparatus includes a light source, an optical scanner, an optical fiber, a light guide system, a photodetector unit, and an image forming unit. The optical scanner scans the fundus of a subject's eye with light from the light source. The optical fiber includes a plurality of optical waveguides. The light guide system guides the light returning from the fundus to the entrance end of the optical fiber. The photodetector unit detects light output from each of at least three regions at the exit end of the optical fiber. The image forming unit forms a first image based on a detection result of light output from a first region of the at least three regions, and a second image based on detection results of light output from two or more regions of the at least three regions other than the first region.

DETAILED DESCRIPTION

Figure 1:
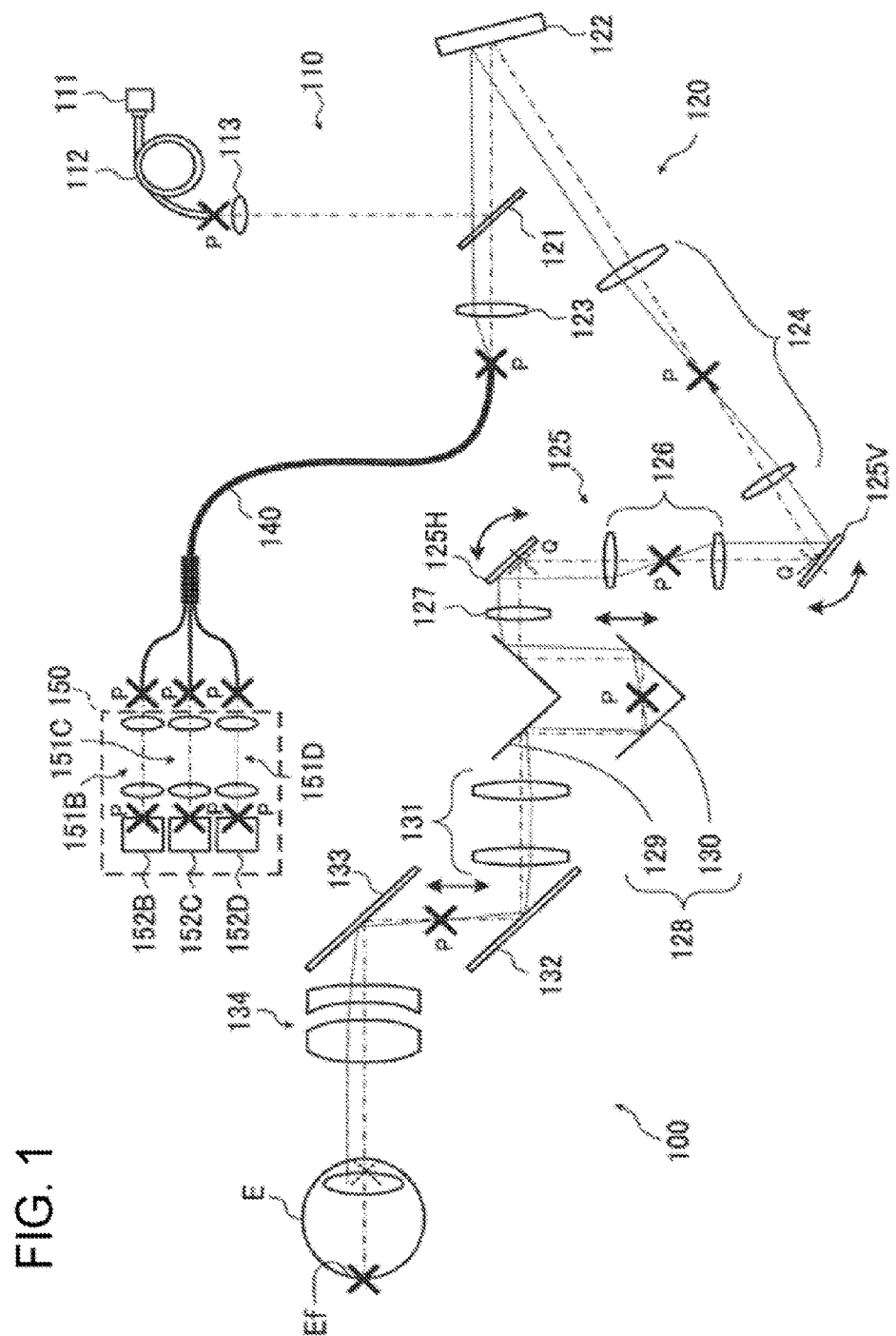
FIG. 1 is a schematic diagram illustrating an example of the configuration of an optical system of a fundus imaging apparatus according to a first embodiment.

Referring now to the drawings, a fundus imaging apparatus is described in detail in some exemplary embodiments. The disclosure of the documents cited herein and any known technology may be incorporated in the following embodiments by reference.

A fundus imaging apparatus is an apparatus configured to irradiate the fundus of the subject's eye with light and receive the light reflected therefrom (fundus reflection light, return light), thereby obtaining an image illustrating the morphology of the fundus. According to the following embodiments, a fundus imaging apparatus includes an optical system of a scanning laser ophthalmoscope, which is configured to scan the fundus of the subject's eye with a laser beam and detect the light reflected from the fundus though a light-receiving device, and is capable of forming a front image of the fundus.

First Embodiment (Optical System)

FIG. 1 is a schematic diagram illustrating an example of the configuration of an optical system of a fundus imaging apparatus according to a first embodiment. FIG. 1 illustrates an example of the configuration of the optical system for dividing, into two, a peripheral light beam around the point image center area in a fundus conjugate position. In FIG. 1, a position optically conjugate with the fundus Ef of the subject's eye E is illustrated as a fundus conjugate position P, and a position optically conjugate with the pupil of the subject's eye E is illustrated as a pupil conjugate position Q.

An optical system 100 includes an irradiation system 110, a light guide system 120, a multi-branch bundle fiber 140, and a detection system 150. The irradiation system 110 includes an optical system configured for irradiating the subject's eye E with light. The light guide system 120 includes an optical system configured for guiding the light from the irradiation system 110 to the subject's eye E, and guiding the light reflected from the subject's eye E to the entrance end of the multi-branch bundle fiber 140. The multi-branch bundle fiber 140 guides the light reflected from the fundus Ef of the subject's eye E to a plurality of exit ends. The detection system 150 detects the light that has been guided by the multi-branch bundle fiber 140 as light of the point image center area in the fundus conjugate point and light of its periphery.

The irradiation system 110 includes a light source 111, an optical fiber 112, and a lens 113. The light source 111 emits a laser beam having a wavelength component(s) selected from, for example, the wavelength range of 500 nm to 900 nm. Examples of the light source 111 include a laser diode (LD), a super-luminescent diode (SLD), a laser-driven light source (LDLS), and the like. The laser beam emitted from the light source 111 is not limited to light of a single wavelength, and may have wavelength components of a certain band width. The light source 111 may emit light having high directivity (i.e., light with small divergence angle).

The optical fiber 112 is connected to the light source 111. The optical fiber 112 guides the laser beam to the light guide system 120. The optical fiber 112 is a single mode fiber. The core diameter of the optical fiber 112 may be substantially equal to the spot diameter of the laser beam emitted from the light source 111. The lens 113 is located at the exit end of the optical fiber 112. The lens 113 collimates the laser beam output from the optical fiber 112 to generate a parallel light beam. The laser beam having passed through the lens 113 are guided to a beam splitter 121 included in the light guide system 120.

The beam splitter 121 is an optical path coupling member to couple the optical path of the irradiation system 110 with the optical path of the light guide system 120. The beam splitter 121 reflects the laser beam having passed through the lens 113 toward a mirror 122, and transmits the light reflected from the fundus of the subject's eye E to guide it to a condenser lens 123.

An optical scanner 125 is located on the subject's eye E side of the mirror 122. A lens system 124 is arranged between the mirror 122 and the optical scanner 125 to adjust the light beam. The optical scanner 125 is used to scan the fundus Ef of the subject's eye E with the laser beams from the light source 111. The optical scanner 125 includes a vertical optical scanner 125V and a horizontal optical scanner 125H. The vertical optical scanner 125V is a mirror whose tilt angle is variable. The tilt of the reflecting surface of the mirror is controlled by a controller 200 (described later). The vertical optical scanner 125V is used for, for example, vertical scanning in the fundus plane. The vertical optical scanner 125V may be a low-speed scanner such as a galvanometer mirror. The horizontal optical scanner 125H is located on the subject's eye E side of the vertical optical scanner 125V. A lens system 126 is arranged between the optical scanners 125V and 125H. The horizontal optical scanner 125H is a mirror whose tilt angle is variable. The tilt of the reflecting surface of the mirror is controlled by the controller 200. The horizontal optical scanner 125H is used for, for example, horizontal scanning in the fundus plane perpendicular to the vertical direction. Either one of the vertical optical scanner 125V and the horizontal optical scanner 125H may be a high-speed scanner such as a resonant mirror, a microelectromechanical systems (MEMS) mirror, or the like. The reflecting surface of the horizontal optical scanner 125H and the reflecting surface of the vertical optical scanner 125V are each arranged in a position (pupil conjugate position) optically conjugate with the pupil of the subject's eye E or a position around there.

A diopter correction mechanism 128 is located on the subject's eye E side of the horizontal optical scanner 125H. A lens 127 is arranged between the horizontal optical scanner 125H and the diopter correction mechanism 128. The diopter correction mechanism 128 is one example of an adjusting means for adjusting the laser beam to be irradiated on the fundus Ef as a substantially point image. The diopter correction mechanism 128 continuously moves the position of the fundus conjugate point according to the refractive power of the subject's eye E. The diopter correction mechanism 128 is provided with V-shaped diopter correction mirrors 129 and 130. By relatively bringing the diopter correction mirror 130 near or far from the diopter correction mirror 129, the focus of the optical system 100 is adjusted to the fundus Ef. There are individual differences in the diopter scale. The position of the diopter compensation mirror 130 is moved such that the focus of the optical system 100 is located on the fundus Ef, i.e., such that the irradiation light is adjusted to be irradiated and condensed on the fundus Ef as a substantially point image, regardless of the differences in the diopter scale. Incidentally, in the diopter correction mechanism 128, the pupil of the subject's eye E is in the conjugate relationship with the infinity, and therefore, the movement of the diopter correction mirror 130 does not change the pupil conjugate relationship in the optical system 100.

Mirrors 132 and 133 are located on the subject's eye E side of the diopter correction mechanism 128. A lens system 131 is arranged between the diopter correction mechanism 128 and the mirrors 132 and 133. An objective lens 134 is arranged on the subject's eye E side of the mirror 133. The objective lens 134 has a structure in which a plurality of lenses is combined in order to suppress aberration (needless to say, it may be formed of a single lens).

The light reflected from the fundus of the subject's eye E travels through the path of the laser beam from the objective lens 134 to the beam splitter 121 in the opposite direction, and is condensed while passing through the condenser lens 123. The optical elements included in the light guide system 120 are arranged such that the condensing position of the condenser lens 123 is located in the fundus conjugate position P or its vicinity. The entrance end of the multi-branch bundle fiber 140 is located in the condensing position of the condenser lens 123 (fundus conjugate position P). The multi-branch bundle fiber 140 is an optical fiber, in which a plurality of fiber cores (optical waveguides) are bundled into one on the entrance end side, and the plurality of fiber cores are divided into a plurality of small bundles on the exit end side.

Figure 2:
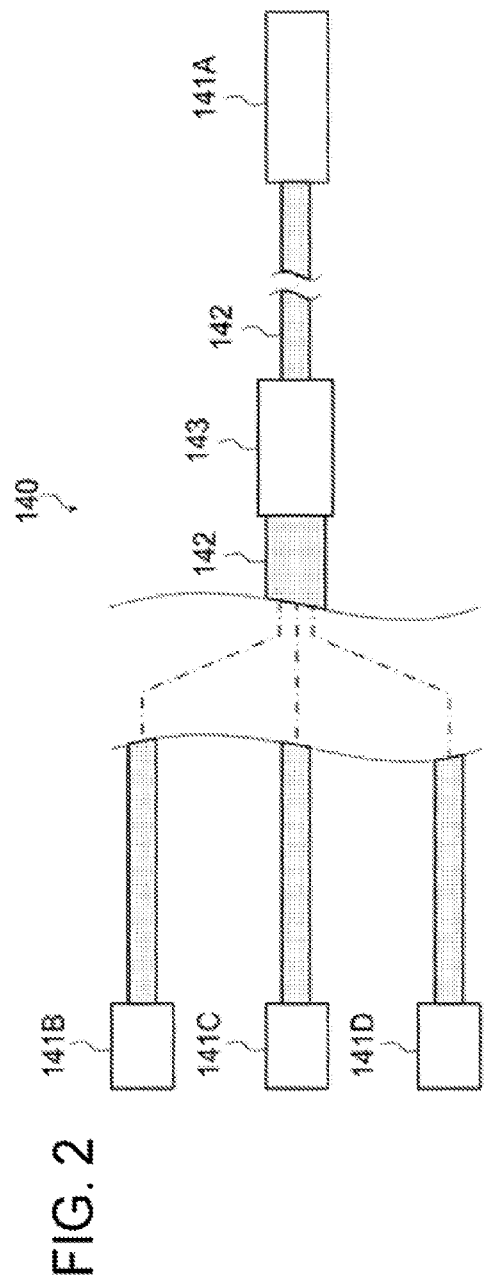
FIG. 2 is a schematic diagram for explaining a multi-branch bundle fiber of the first embodiment.
Figure 3:
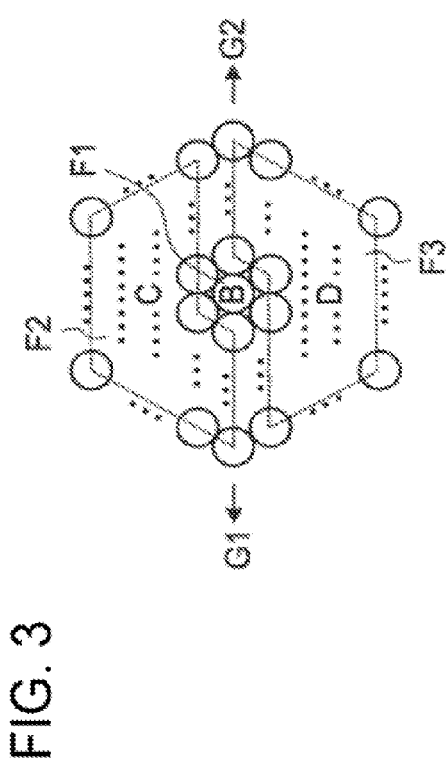
FIG. 3 is a schematic diagram for explaining the multi-branch bundle fiber of the first embodiment.

FIGS. 2 and 3 are explanatory diagrams illustrating the multi-branch bundle fiber 140 according to the embodiment. FIG. 2 schematically illustrates an example of the configuration of the multi-branch bundle fiber 140 having three branches. FIG. 3 schematically illustrates an example of the arrangement of the fiber cores at the entrance end face of the multi-branch bundle fiber 140 of FIG. 2.

A connector 141A is provided on the entrance end side of the multi-branch bundle fiber 140, while connectors 141B, 141C, and 141D are provided on the exit end side. The connector 141A is connected to one end of a flexible tube 142 such as a stainless used steel (SUS) flexible tube through which 2×N+1 pieces of fiber cores are inserted (here, N is a positive integer). Each of the connectors 141A to 141D is detachably connected to a corresponding connector. Each of the connectors 141A to 141D is, for example, an FC connector. This makes it possible to maintain the proper connection state by the screw fixing, and also to facilitate the replacement of the multi-branch bundle fiber 140 with another bundle fiber of different dividing manner and a different number of divisions.

While being held by a branching hardware 143, 2×N+1 pieces of fiber cores are divided into three small bundles consisting of one fiber core (the center core) and two types of N pieces of fiber cores. Each of the small bundles is also inserted through a flexible tube such as a SUS flexible tube. The connector 141B is connected to the other end of the flexible tube through which one fiber core is inserted. The connectors 141C and 141D are each connected to the other end of the flexible tube through which N pieces of fiber cores are inserted. Such a structure enables each of the connectors 141B to 141D to be connected to a connector arranged in any position.

As illustrated in FIG. 3, one center core (a single fiber core), the other end of which is connected to the connector 141B, is arranged in the central region F1 at the entrance end face of the multi-branch bundle fiber 140. The entrance end of the center core is arranged in the optical axis of the light guide system 120. N pieces of fiber cores, which are connected to the connector 141C, are arranged in the peripheral divisional region F2 at the entrance end face of the multi-branch bundle fiber 140. N pieces of fiber cores, which are connected to the connector 141D, are arranged in the peripheral divisional region F3 at the entrance end face of the multi-branch bundle fiber 140. Thereby, a light beam incident on the central region F1 at the entrance end face of the multi-branch bundle fiber 140 is guided to the connector 141B through the center core. A light beam incident on the peripheral divisional region F2 is guided to the connector 141C through N fiber cores. Similarly, a light beam incident on the peripheral divisional region F3 is guided to the connector 141D through N fiber cores.

In the entrance end face of the multi-branch bundle fiber 140, except the center core in the central region F1, 2×N pieces of fiber cores are divided into a plurality of small bundles in an arbitrary manner. That is, it is not limited by the shape of the peripheral divisional regions in the entrance end face. For example, fiber cores other than the center core are divided left and right into two, divided vertically and horizontally into four, or divided radially into eight.

Besides, although FIG. 2 and FIG. 3 illustrate an example in which fiber cores are divided into two small bundles, the number of divisions into small bundles may be three or more. The small bundles are not necessarily formed of the same number of fiber cores. Each of the fiber cores of the multi-branch bundle fiber 140 may be a single mode fiber, or it may be a multimode fiber. The diameter of the center core may be different from that of other fiber cores.

The entrance end side (the connector 141A) of the multi-branch bundle fiber 140 may be rotatable about its optical axis. In this case, the fundus imaging apparatus of the embodiment includes a rotating mechanism (second mechanism) for rotating the entrance end side of the multi-branch bundle fiber 140. For example, the user may manually rotate the connector 141A around the optical axis of the center core by using the rotating mechanism. Thereby, the user can change the dividing direction of the peripheral divisional regions illustrated in FIG. 3 while viewing a phase contrast image (described later). This facilitates the adjustment of the dividing direction for obtaining a desired image.

The connector 141A may be provided with keys (e.g., keys G1 and G2 in FIG. 3) in a position corresponding to the boundary of the peripheral divisional regions. With this, the user can rotate the connector 141A while checking the dividing direction of the peripheral divisional regions by the location of the keys.

As illustrated in FIG. 1, the detection system 150 is located at the exit end of the multi-branch bundle fiber 140 as described above. The detection system 150 detects each light output from the exit end of the multi-branch bundle fiber 140. The exit end of the multi-branch bundle fiber 140 is divided into at least three regions. Therefore, the detection system 150 is capable of detecting light output from each of the at least three regions at the exit end of the multi-branch bundle fiber 140. In this embodiment, the detection system 150 includes a relay optical system and a photodetector corresponding to each of the exit ends of the multi-branch bundle fiber 140. In the present example, the detection system 150 includes relay optical systems 151B, 151C and 151D, and photodetectors 152B, 152C and 152D.

The relay optical system 151B and the photodetector 152B are provided correspondingly to the connector 141B. The relay optical system 151B is an optical system configured to relay the fundus conjugate point of the light output from the connector 141B. The photodetector 152B is a photo-detecting element configured to detect the light output from the connector 141B. The photo-detecting surface of the photodetector 152B is arranged in the fundus conjugate position. The photodetector 152B is made of, for example, an avalanche photodiode (APD) or a photomultiplier tube (PMT). The detection result of fundus reflection light from the fundus Ef of the subject's eye E obtained by the photodetector 152B is used for forming an SLO image (a confocal image) as the detection result of light in the point image center area at the fundus conjugate point.

The relay optical system 151C and the photodetector 152C are provided correspondingly to the connector 141C. The relay optical system 151C is an optical system configured to relay the fundus conjugate point of the light output from the connector 141C. The photodetector 152C is a photo-detecting element configured to detect the light output from the connector 141C. The photo-detecting surface of the photodetector 152C is arranged in the fundus conjugate position. The photodetector 152C has the same configuration as that of the photodetector 152B.

The relay optical system 151D and the photodetector 152D are provided correspondingly to the connector 141D. The relay optical system 151D is an optical system configured to relay the fundus conjugate point of the light output from the connector 141D. The photodetector 152D is a photo-detecting element configured to detect the light output from the connector 141D. The photo-detecting surface of the photodetector 152D is arranged in the fundus conjugate position. The photodetector 152D has the same configuration as that of the photodetector 152B. The detection result of fundus reflection light from the fundus Ef of the subject's eye E obtained by the photodetectors 152C and 152D is used for forming a phase contrast image (a non-confocal image) as the detection result of light in the peripheral area around the point image center area at the fundus conjugate point.

The multi-branch bundle fiber 140 is an example of the "optical fiber" of the embodiment. The detection system 150 is an example of the "photodetector unit" of the embodiment. The central region F1 is an example of the "first region" of the embodiment. The SLO image is an example of the "first image" of the embodiment. The phase contrast image is an example of the "second image" of the embodiment.

(Processing System)

Figure 4:
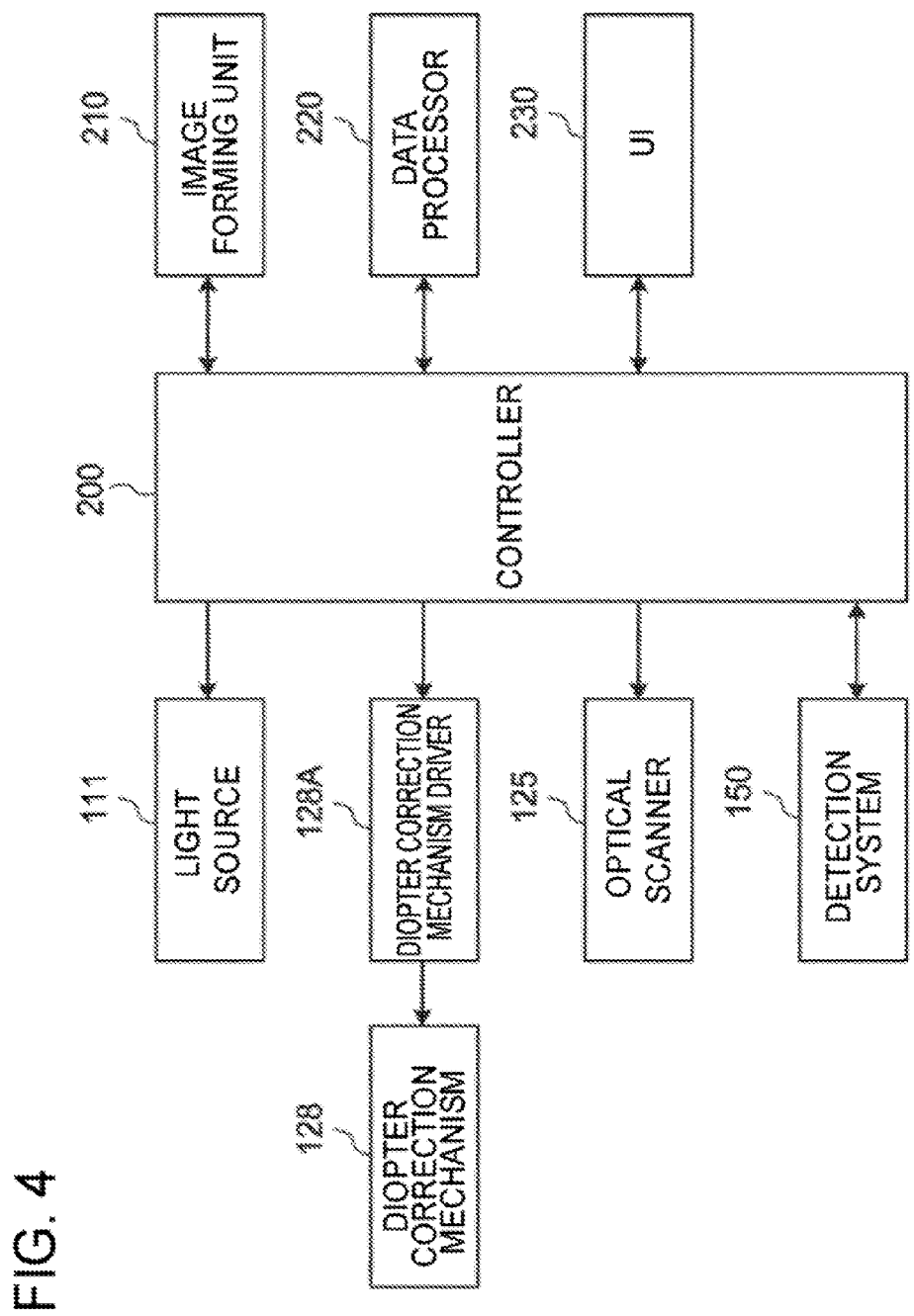
FIG. 4 is a schematic diagram illustrating an example of the configuration of a processing system of the fundus imaging apparatus of the first embodiment.

FIG. 4 illustrates an example of the configuration of a processing system of the fundus imaging apparatus according to the first embodiment. In FIG. 4, like reference numerals designate like parts as in FIGS. 1 to 3. The same description may not be repeated below.

The controller 200 is the center of the processing system of the fundus imaging apparatus of the first embodiment. The controller 200 controls each part of the fundus imaging apparatus. The controller 200 includes a microprocessor and storage. The storage stores, in advance, a computer program for controlling the fundus imaging apparatus. The computer program includes, for example, light source control program, diopter correction mechanism control program, optical scanner control program, detection system control program, image forming program, data processing program, display control program, program for user interface, and the like. The microprocessor operates according to the computer programs, and thereby the controller 200 performs the control operation.

Control for the optical system includes control of the light source 111, control of the optical scanner 125, control of the diopter correction mechanism 128 via a diopter correction mechanism driver 128A, control of the detection system 150, and the like. The control of the light source 111 may include turning on and off the light source, adjustment of the amount of light, adjustment of an aperture, and the like. The control of the optical scanner 125 may include control of the scanning position and the scanning area by means of the vertical optical scanner 125V, control of the scanning position and the scanning area by means of the horizontal optical scanner 125H, and the like. The control of the diopter correction mechanism 128 may include driving control of the diopter correction mechanism driver 128A according to the diopter scale, and the like. The control of the detection system 150 may include adjustment of exposure, adjustment of gain, adjustment of imaging rate, and the like.

An image forming unit 210 forms an image based on the detection result of the fundus reflection light from the fundus Ef of the subject's eye E obtained by the detection system 150. The image forming unit 210 forms an SLO image based on the detection result of the light output from the center core in the central region F1 obtained by the photodetector 152B. For example, the image forming unit 210 forms image data of the SLO image based on a light-receiving signal received from the photodetector 152B and a pixel position signal received from the controller 200.

In parallel with the processing of forming the SLO image, the image forming unit 210 forms a phase contrast image based on the detection result of the light output from fiber cores in the peripheral divisional regions F2 and F3 obtained by the photodetectors 152C and 152D. For example, the image forming unit 210 performs signal processing on signals received from the photodetectors 152C and 152D, and forms image data of the phase contrast image based on the result of the signal processing and a pixel position signal received from the controller 200. For example, when a detection signal obtained by the photodetector 152C is represented by Ic and a detection signal obtained by the photodetector 152D is represented by Id, the phase contrast image can be obtained by calculating the following: $(Ic-Id)/(Ic+Id)$.

If the peripheral divisional region is divided into three or more regions, the image forming unit 210 is capable of forming the phase contrast image based on the detection results of the light output from two or more regions other than the central region F1.

Figure 5:
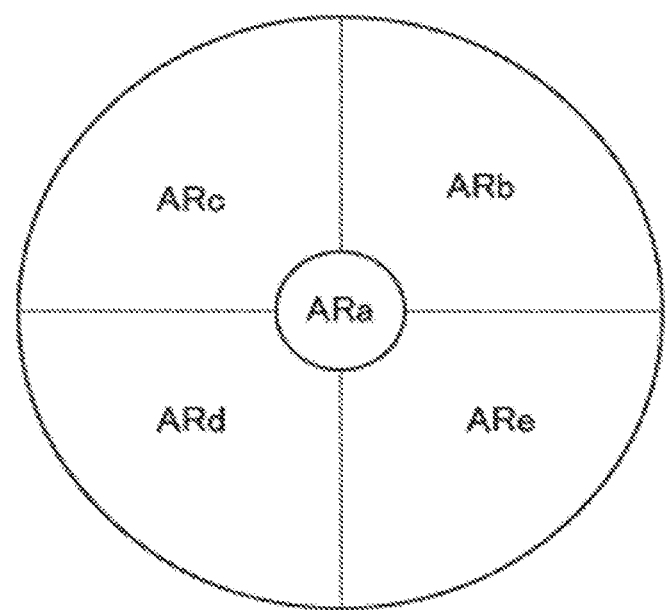
FIG. 5 is a schematic diagram for explaining the operation of the fundus imaging apparatus of the first embodiment.

Further, when the entrance end face of the multi-branch bundle fiber 140 is divided into four or more regions excluding the central region (i.e., the entrance end face has five or more regions), the image forming unit 210 can form a plurality of types of phase contrast images based on the detection results of light emitted from the four or more regions. In this case, the detection system 150 detects the light output from each of five or more regions in the exit end of the multi-branch bundle fiber 140. The image forming unit 210 forms two or more different phase contrast images based on the detection results of the light output from the four or more regions other than the central region among the five or more regions. For example, as illustrated in FIG. 5, it is assumed that the entrance end surface of the multi-branch bundle fiber 140 is divided into a central region ARa and four regions ARb, ARc, ARd and ARe. When detection signals obtained by corresponding photodetectors of the regions ARb, ARc, ARd and ARe are represented by Ib, Ic, Id and Ie, respectively, the image forming unit 210 forms a first phase contrast image by calculating the value of Expression (1). The first phase contrast image is an image obtained by dividing a peripheral light beam around the point image center area at the fundus conjugate position into two in the vertical direction.

$$\frac{(Ib + Ic) - (Id + Ie)}{(Ib + Ic) + (Id + Ie)} \quad (1)$$

Further, the image forming unit 210 forms a second phase contrast image by calculating the value of Expression (2). The second phase contrast image is an image obtained by dividing a peripheral light beam around the point image center area at the fundus conjugate position into two in the lateral direction.

$$\frac{(Ib + Ie) - (Ic + Id)}{(Ib + Ie) + (Ic + Id)} \quad (2)$$

Further, the image forming unit 210 can form a plurality of phase contrast images different in the dividing direction, the number of divisions or the like for the peripheral divisional regions from one another by changing the combination of the peripheral divisional regions. In this case, it is possible to change the dividing direction, the number of divisions or the like of the peripheral divisional regions without rotating the entrance end side of the multi-branch bundle fiber 140.

A data processor 220 performs various types of data processing. As the data processing, for example, the data processor 220 performs processing on image data formed by the image forming unit 210 or another device. Examples of the processing include various types of image processing and diagnosis support processing such as image evaluation based on the image data.

A user interface (UI) 230 has a function for interchanging information between the user and the fundus imaging apparatus. The user interface 230 includes a display device and an operation device (input device). The display devices may include a display part provided in the fundus imaging apparatus, and it may include another display device. The operation device includes various hardware keys and/or software keys. At least part of the display device and at least part of the operation device may be configured integrally. One example of this is the touch panel display.

There may be provided a drive unit configured to drive a rotating mechanism that rotates the entrance end side of the multi-branch bundle fiber 140. In this case, the controller 200 is capable of controlling the driver so as to automatically rotate the entrance end side (the connector 141A) of the multi-branch bundle fiber 140.

Besides, there may be provided a first mechanism configured to change the relative position between the entrance end of the multi-branch bundle fiber 140 and the light guide system 120. The first mechanism is capable of changing the relative position between the center core of the multi-branch bundle fiber 140 and the optical axis of the light guide system 120. For example, the controller 200 may control the first mechanism based on the detection result of the light output from the central region F1 (the detection result obtained by the photodetector 152B). Thereby, it is possible to shorten the time required for alignment.

In the fundus imaging apparatus including the configuration described above, a laser beam, which is fundus irradiation light emitted from the light source 111, is reflected by the beam splitter 121 toward the mirror 122. The laser beam reflected by the mirror 122 is used as scanning light by the optical scanner 125. The laser beam deflected by the horizontal optical scanner 125H is guided to the objective lens 134 through the diopter correction mechanism 128 and the mirrors 132 and 133. Then, the laser beam is irradiated onto the fundus Ef of the subject's eye E through the objective lens 134. At that time, the diopter correction mechanism 128 is controlled such that the focus of the optical system 100 is adjusted to the fundus Ef of the subject's eye E.

The fundus reflection light, which is the light reflected from the fundus Ef of the subject's eye E, travels through the path of the fundus irradiation light in the opposite direction, and is led to the beam splitter 121. Having passed through the beam splitter 121, the fundus reflection light is guided to the entrance end of the multi-branch bundle fiber 140. At the entrance end of the multi-branch bundle fiber 140, there are arranged the entrance end of the center core for guiding light beams in the point image center area at the fundus conjugate position, and the entrance ends of the fiber cores of two or more small bundles for guiding light beams around the point image center area. A light beam incident on the entrance end of the center core is guided to the photodetector 152B, and used to form an SLO image. The light beams incident on the entrance ends of the fiber cores of the two or more small bundles are guided to, for example, the photodetectors 152C and 152D, and used to form a phase contrast image.

(Effects)

Described below are the effects of the fundus imaging apparatus of the embodiment.

According to the embodiment, the fundus imaging apparatus includes a light source (the light source 111), an optical scanner (the optical scanner 125), an optical fiber (the multi-branch bundle fiber 140), a light guide system (the light guide system 120), a photodetector unit (the detection system 150), and an image forming unit (the image forming unit 210). The optical scanner is configured to scan the fundus (fundus Ef) of the subject's eye (subject's eye E) with light from the light source. The optical fiber includes a plurality of optical waveguides (center core, fiber cores). The light guide system is configured to guide fundus reflection light, which is light reflected from the fundus, to the entrance end of the optical fiber. The photodetector unit is configured to detect light output from each of at least three regions at the exit end of the optical fiber. The image forming unit is configured to form a first image (SLO image) based on the detection result of light output from a first region (central region F1) of the at least three regions. The image forming unit is also configured to form a second image (phase contrast image) based on the detection results of light output from two or more regions (peripheral divisional regions F2, F3) of the at least three regions other than the first region.

With this configuration, although it is required to arrange the position of the entrance end and the position of the exit end of the optical fiber with high accuracy, there is no need of providing a light beam dividing element, and, for example, it is possible to obtain a light beam in the point image center area and light beams in the periphery of the point image center area separately. In the conventional technology, an increase in the number of divisions of the light beam in the periphery of the point image center area requires to form as many fundus conjugate points as the number of divisions. This results in an enlarged optical system. On the other hand, in the embodiment, the number of divisions is determined according to the number of branches of the optical fiber. Thus, there is no need to increase the number of fundus conjugate point.

Besides, the degree of freedom in the arrangement of the optical system is increased within the range of the length of the optical fiber. Thus, space saving can be achieved. Further, with respect to the arrangement of the optical waveguide at the entrance end face of the optical fiber, it is possible to freely design optical waveguides that constitute small bundles, the number of divisions, and the like. Therefore, diversity can be easily provided to the division of peripheral light beams around the point image center area. Moreover, regardless of the number of divisions, the light for forming the first image and the light for forming the second image can be detected simultaneously. This eliminates the need to perform registration of the two images. This facilitates the superimposition of the first and second images, for example.

In the fundus imaging apparatus of the embodiment, the entrance end of at least one of the optical waveguides included in the first region may be arranged on the optical axis of the light guide system.

With this configuration, it becomes possible to detect the light beam guided by the optical waveguide included in the first area as a light beam in the point image center area.

The fundus imaging apparatus of the embodiment may further include a first mechanism and a controller (the controller 200). The first mechanism is configured to change the relative position between the entrance end of the optical fiber and the light guide system. The controller is configured to control the first mechanism based on the detection result of the light output from the first region.

With this configuration, for example, as well as detecting an increase or decrease in the amount of the light output from the optical waveguide of the first region, it is possible to align the entrance end of the optical fiber in a desired position (e.g., a fundus conjugate position) with high accuracy. If this alignment can be performed properly for the first region, accurate alignment can be carried out for other regions. Thus, even if the number of divisions is increased, it is possible to shorten the time required for the alignment.

The fundus imaging apparatus of the embodiment may further include a second mechanism. The second mechanism is configured to rotate the entrance end side of the optical fiber.

With this configuration, the rotation of the entrance end side of the optical fiber can be facilitated. Thereby, for example, it becomes possible to divide peripheral light beams around the point image center area in a desired direction with reference to the phase contrast image.

Further, in the fundus imaging apparatus of the embodiment, the photodetector unit may be configured to detect the light output from each of five or more regions at the exit end. In addition, the image forming unit may form two or more different second images based on the detection results of the light output from four or more regions of the five or more regions other than the first region.

With this configuration, the method of dividing a light beam in the periphery of the point image center area, the number of divisions, or the like can be easily changed by changing the combination of four or more regions other than the first region. Thus, various phase contrast images can be acquired.

In the fundus imaging apparatus of the embodiment, the entrance end of the optical fiber may be located in a position optically conjugate with the fundus or near the position.

With this configuration, it becomes possible to detect the light beam guided by the optical waveguide included in the first area as a light beam in the point image center area at the fundus conjugate position.

In the fundus imaging apparatus of the embodiment, the photodetector unit may include three or more photodetectors (the photodetectors 152B to 152D) configured to detect the light output from each of the at least three regions, respectively.

With this configuration, it is possible to separately detect the light beams in the periphery of the point image center area.

Second Embodiment

In the first embodiment, an example is described in which the optical system of the fundus imaging apparatus has an SLO optical system. However, the optical system of the fundus imaging apparatus of the embodiment is not limited to the SLO optical system. According to a second embodiment, the optical system of the fundus imaging apparatus is provided with an adaptive optics scanning laser ophthalmoscope (AO-SLO).

The fundus imaging apparatus of the second embodiment has basically the same configuration as that of the fundus imaging apparatus of the first embodiment except the presence of an additional adaptive optical system. In the following, the fundus imaging apparatus of the second embodiment is described focusing on differences from the first embodiment.

Figure 6:
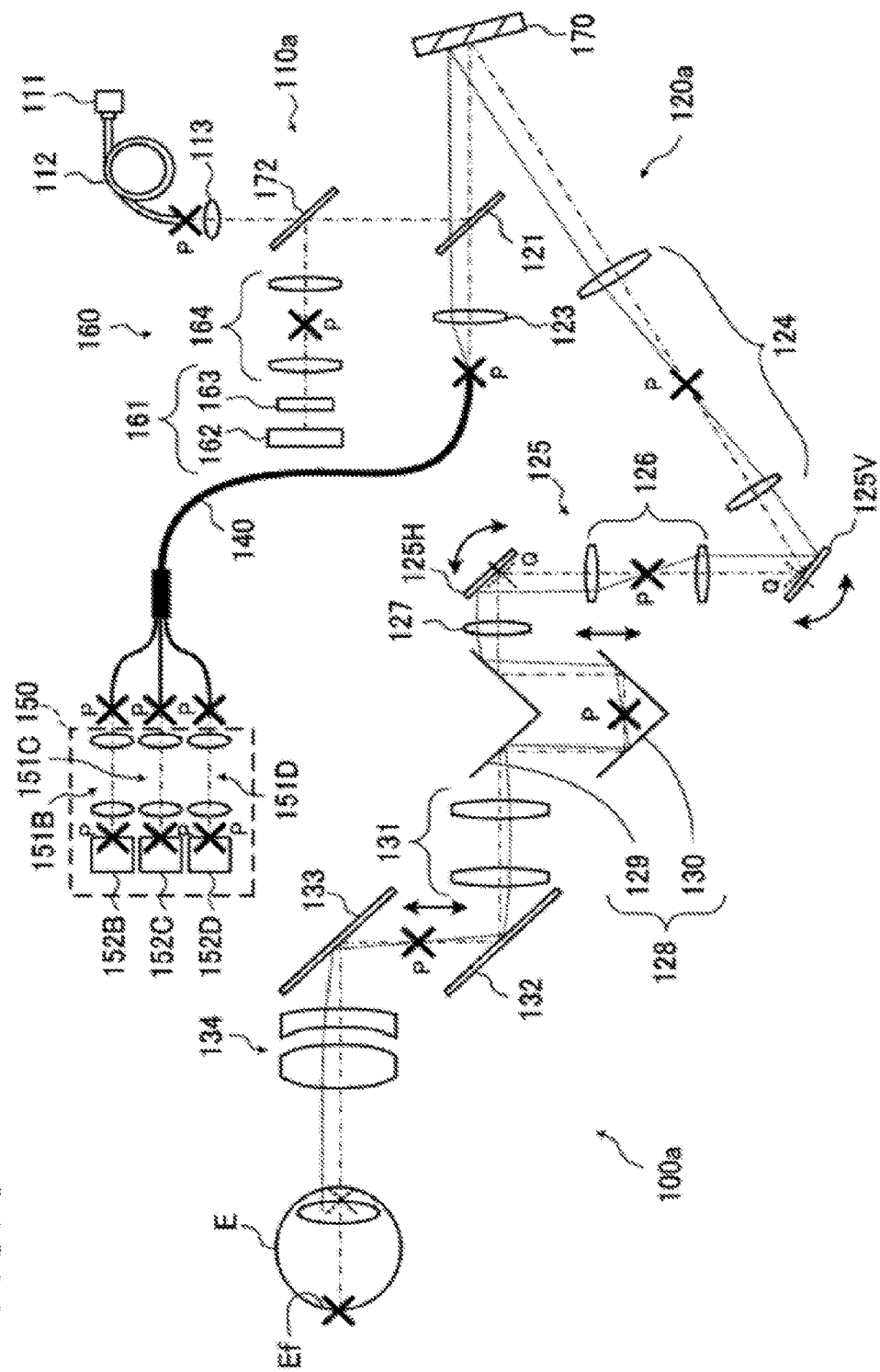
FIG. 6 is a schematic diagram illustrating an example of the configuration of an optical system of a fundus imaging apparatus according to a second embodiment.

FIG. 6 illustrates an example of the configuration of the optical system of the fundus imaging apparatus according to the second embodiment. In FIG. 6, like reference numerals designate like parts as in FIG. 1. The same description may not be repeated.

An optical system 100*a* of the second embodiment is different from the optical system 100 of the first embodiment in that: an irradiation system 110*a* is provided in place of the irradiation system 110; a light guide system 120*a* is provided in place of the light guide system 120; and a wave front detection system 160 is additionally provided. The light guide system 120*a* is provided with a deformable mirror 170 in place of the mirror 122. In the irradiation system 110*a*, a half mirror 172 is arranged between the lens 113 and the beam splitter 121, and the fundus reflection light from the fundus Ef of the subject's eye E is guided to the wave front detection system 160.

The half mirror 172 is a light amount splitting mirror for branching the irradiation system 110*a* and the wave front detection system 160. The wave front detection system 160 is an optical system for detecting wave front information from the light (detection light) reflected from the fundus Ef of the subject's eye E. The half mirror 172 transmits a part of a laser beam emitted from the light source 111 to the beam splitter 121 side, and reflects a part of the detection light incident from the beam splitter 121 side toward the wave front detection system 160. Incidentally, the branching ratio of the half mirror 172 is not limited to 1:1.

The wave front detection system 160 includes a wave front detector 161 and a pair of lenses 164. The wave front detector 161 may be a Shack-Hartmann sensor including a CCD 162 as an imaging device and a lens array 163 located in front of the CCD 162. The lens array 163 is formed of small lenses which are arranged in a grid pattern. The lens array 163 divides the incident light into a number of light beams, and condenses each of the light beams. The focal points of the lens array 163 are captured by the CCD 162. By analyzing the focal positions of the lenses, it is possible to detect the wave front aberration of the light incident on the lens array 163. That is, by observing a reflection image from the fundus Ef of the subject's eye E through the lens array 163, it is possible to detect the disturbance of a wave front in the reflection image. The image captured by the CCD 162 is sent to an image analyzer, which is provided in a controller 200a, the image forming unit 210, the data processor 220, or the like. The image analyzer analyzes the disturbance of the wave front. Thus, a control signal (feedback signal), which is based on the result of the analysis, is sent to the deformable mirror 170.

A confocal diaphragm may be arranged in the fundus conjugate position P between the lenses 164.

The beam splitter 121 is a light amount splitting mirror for branching the irradiation system 110a, the detection system 150, and the multi-branch bundle fiber 140. The deformable mirror 170 is located on the subject's eye E side of the beam splitter 121. The deformable mirror 170 is used for wave front correction. The deformable mirror 170 is a mirror that can deform the shape of the surface by a plurality of actuators. The deformable mirror 170 is driven by a control signal based on the analysis result of an image formed with the use of a detection result obtained by the CCD 162. For example, if there is a distortion (distortion of the wave front) in a captured image based on the detection result of the CCD 162, the shape of the surface of the deformable mirror 170 is deformed to reduce the distortion. That is, the surface shape of the deformable mirror 170 is changed so as to reduce the distortion of the image of the fundus Ef based on the detection results obtained by the photodetectors 152B to 152D under the feedback control. Thus, the distortion of the image of the fundus Ef is suppressed.

Figure 7:
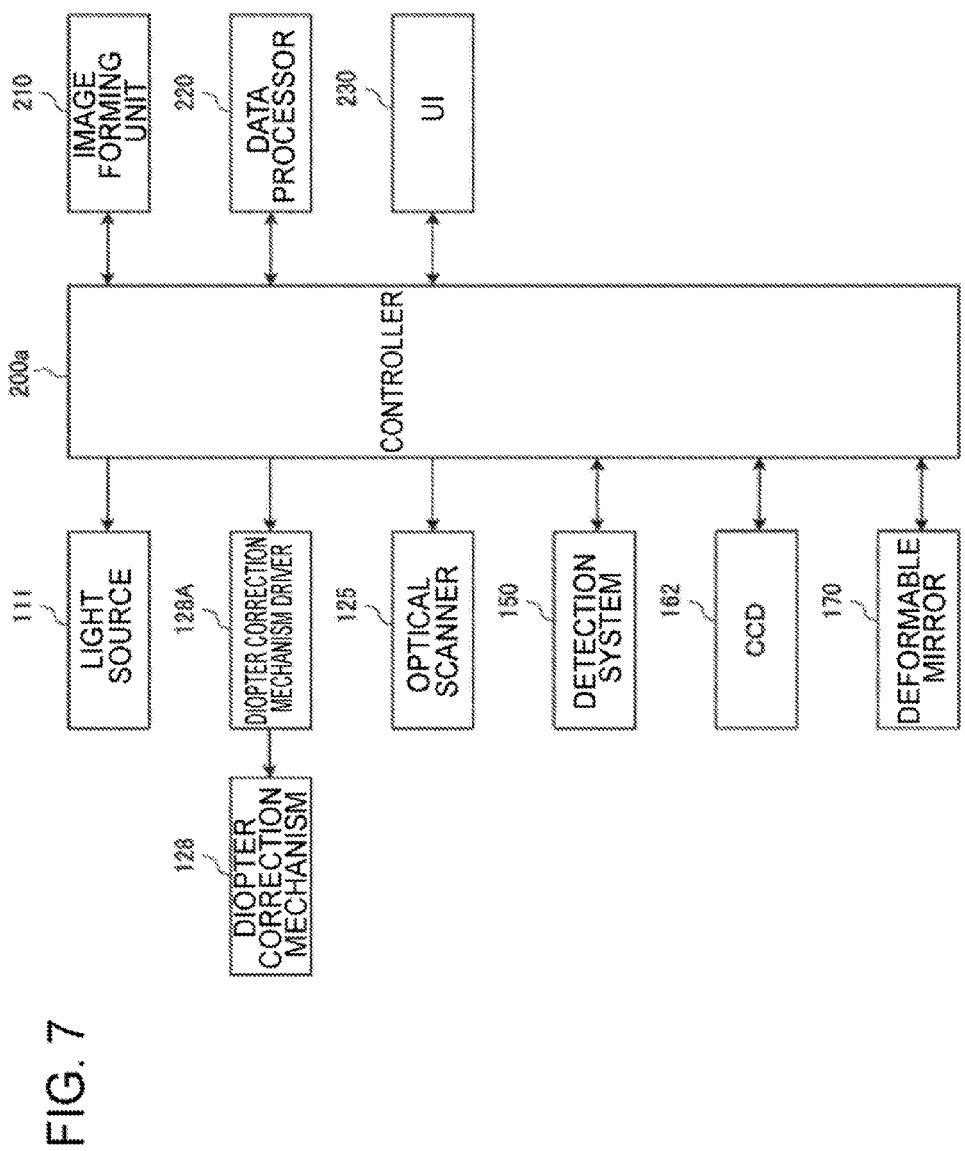
FIG. 7 is a schematic diagram illustrating an example of the configuration of a processing system of the fundus imaging apparatus of the second embodiment.

FIG. 7 illustrates an example of the configuration of a processing system of the fundus imaging apparatus according to the second embodiment. In FIG. 7, like reference numerals designate like parts as in FIGS. 4 and 6. The same description may not be repeated.

In addition to the same control as performed by the controller 200, the controller 200a performs control for the CCD 162, control for the deformable mirror 170. Examples of the control for the CCD 162 include adjustment of exposure, adjustment of gain, adjustment of imaging rate, and the like. Examples of the control for the deformable mirror 170 include drive control for a plurality of actuators according to the detection result obtained by the CCD 162.

In the second embodiment, having reached the beam splitter 121, the fundus reflection light from the fundus Ef of the subject's eye E is branched; one is led to the half mirror 172, and the other is led to the condenser lens 123. The half mirror 172 reflects the fundus reflection light toward the wave front detection system 160. The wave front detection system 160 detects the light by the wave front detector 161. When the wave front detector 161 detects the state of the wave front of the fundus reflection light, the controller 200a performs control for changing the surface shape of the deformable mirror 170 such that the distortion is corrected.

With the fundus imaging apparatus having the configuration described above, the same effects as in the first embodiment can be achieved. Further, an SLO image, which is compensated by the adaptive optical system, can be acquired.

Third Embodiment

According to a third embodiment, the optical system of the fundus imaging apparatus is provided with an SLO optical system and an optical coherence tomography (OCT) optical system.

The fundus imaging apparatus of the third embodiment has basically the same configuration as that of the fundus imaging apparatus of the first embodiment except the presence of an additional OCT optical system. In the following, the fundus imaging apparatus of the third embodiment is described focusing on differences from the first embodiment.

Figure 8:
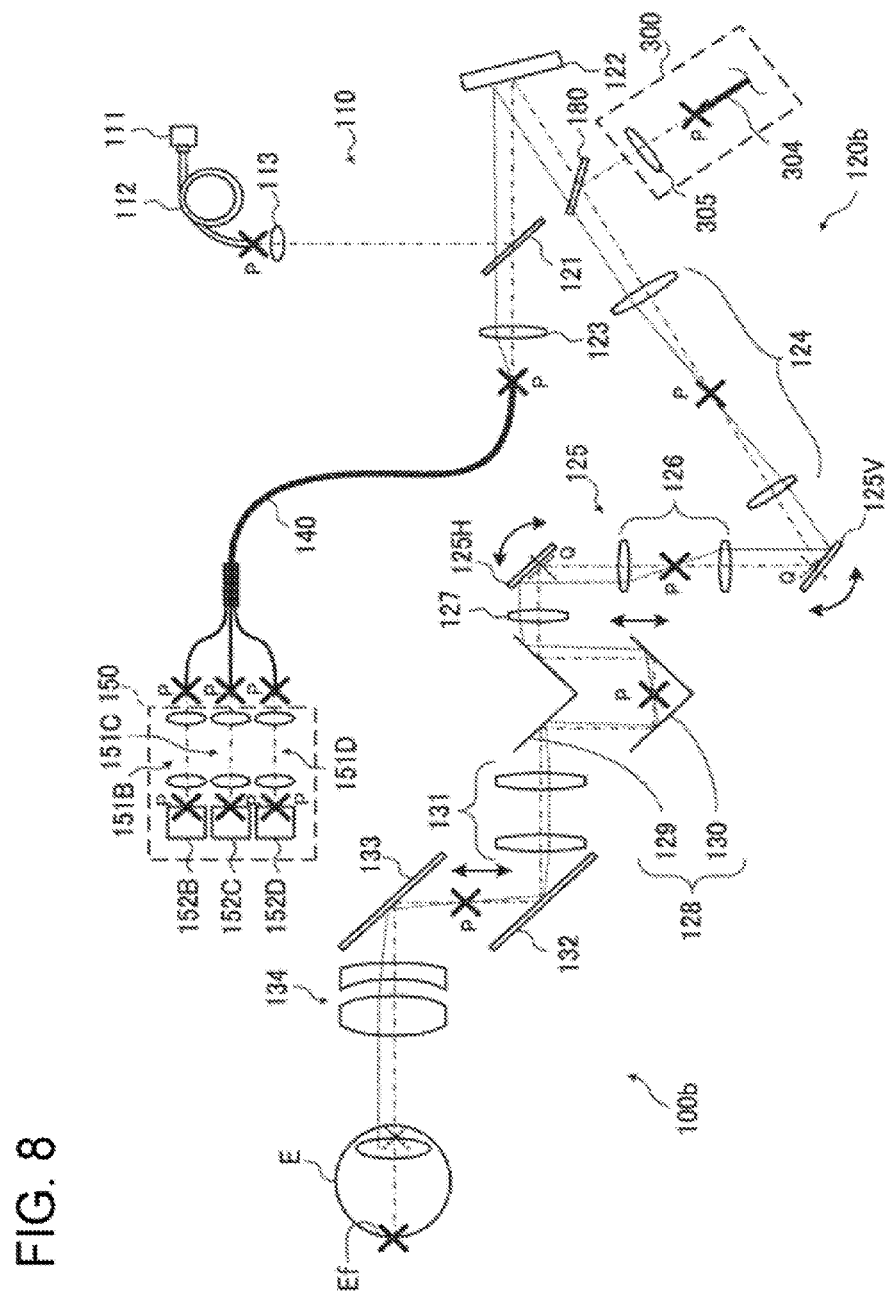
FIG. 8 is a schematic diagram illustrating an example of the configuration of an optical system of a fundus imaging apparatus according to a third embodiment.
Figure 9:
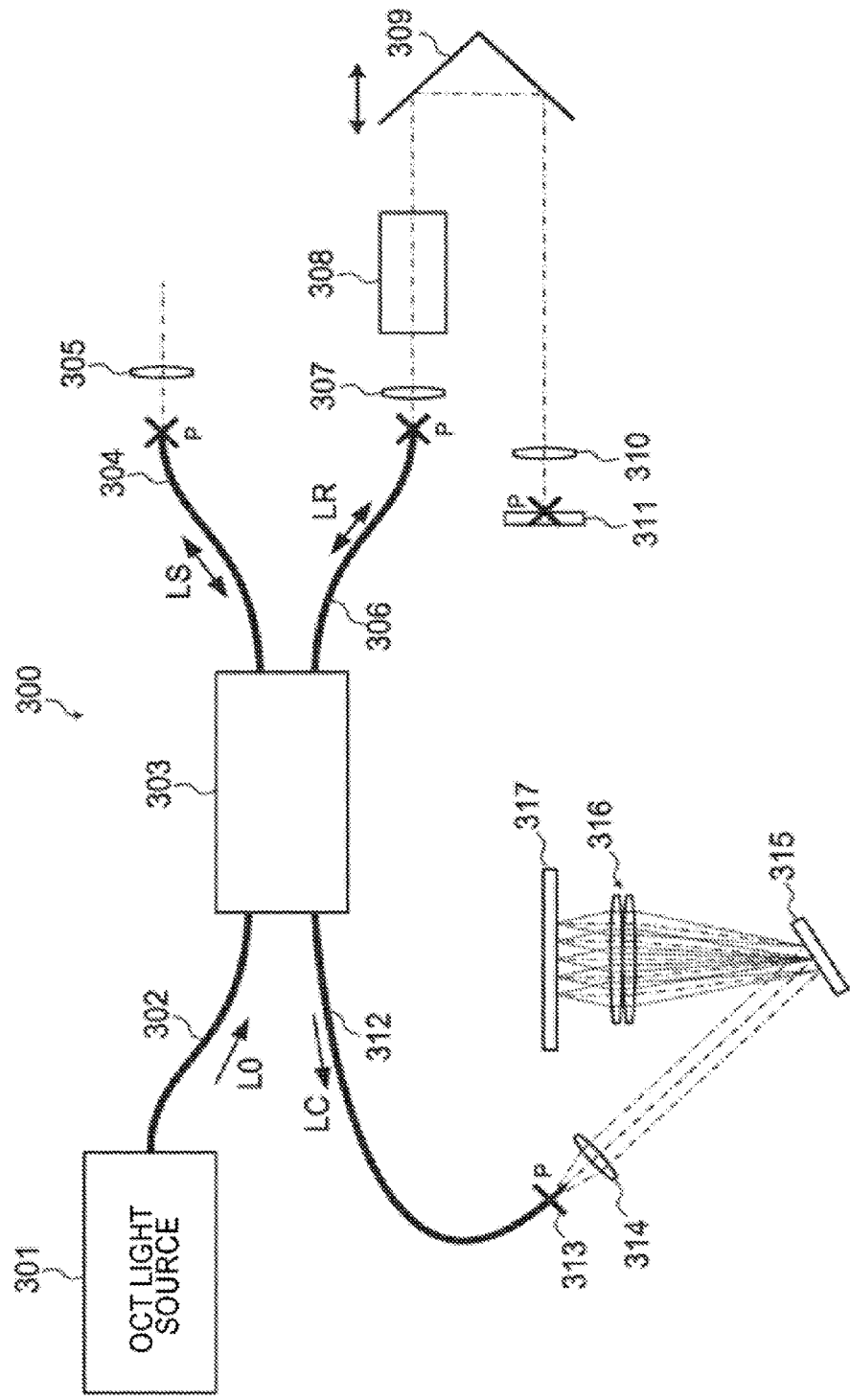
FIG. 9 is a schematic diagram illustrating an example of the configuration of an optical system of the fundus imaging apparatus of the third embodiment.

FIGS. 8 and 9 illustrate an example of the configuration of the optical system of the fundus imaging apparatus according to the third embodiment. FIG. 8 illustrates an example of the overall configuration of an optical system 100b of the third embodiment. FIG. 9 illustrates an example of the configuration of an OCT optical system 300 of FIG. 8. In FIG. 8, like reference numerals designate like parts as in FIG. 1. The same description may not be repeated.

The optical system 100b of the third embodiment is different from the optical system 100 of the first embodiment in that a light guide system 120b is provided in place of the light guide system 120, and that the OCT optical system 300 is additionally provided. In the light guide system 120b, a dichroic mirror 180 is arranged between the mirror 122 and the lens system 124. The dichroic mirror 180 transmits a laser beam from the light source 111, and transmits the fundus reflection light from the fundus Ef of the subject's eye E. Besides, the dichroic mirror 180 reflects measuring light LS from the OCT optical system 300 (described later) toward the optical scanner 125, and also reflects the measuring light LS returning from the subject's eye E to the OCT optical system 300.

The OCT optical system 300 is provided with an optical system for acquiring an OCT image of the measurement site such as the fundus Ef. This optical system has the same configuration as the conventional Fourier domain OCT device. More specifically, this optical system is configured to: divide light (low coherence light) emitted from the OCT light source into reference light LR and measuring light LS; superpose return light of the measuring light LS returning from the fundus Ef on the reference light LR, which has traveled through the reference light path, to generate interference light LC; and detect the spectral components of the interference light LC. The result of the detection (detection signal) is sent to an image forming unit 210c.

An OCT light source 301 outputs broadband, low-coherence light L0. The low-coherence light L0 has, for example, a wavelength band different from that of the laser beam emitted from the light source 111. For example, the low-coherence light L0 has a wavelength component of 1000 nm with the wavelength width of about 50 nm. The OCT light source 301 includes a light emitting device, such as a super luminescent diode (SLD). Although OCT of the spectral domain type is particularly described in this embodiment, the swept source OCT can also be used. When the swept source OCT is employed, a wavelength variable laser light source (wavelength tunable laser light source) is used as the OCT light source 301. Generally, the configuration of the OCT light source 301 is selected as appropriate according to the type of optical coherence tomography.

The low coherence light L0 output from the OCT light source 301 is guided by an optical fiber 302 to a fiber coupler 303, and divided into the measuring light LS and the reference light LR.

The measuring light LS is guided by an optical fiber 304, and collimated into a parallel light beam by a collimator lens 305. The optical path of the measuring light LS is coupled to the optical path of the aforementioned SLO optical system by the dichroic mirror 180. Having traveled through the optical path, the measuring light LS is irradiated onto the fundus Ef. The measuring light LS is scattered and reflected at, for example, the measurement site such as the fundus Ef. The scattered and reflected light may be sometimes referred to as return light of the measuring light LS. The return light of the measuring light LS travels through the same path in the opposite direction, and is thereby guided to the fiber coupler 303.

The reference light LR is guided by an optical fiber 306, and collimated into a parallel light beam by a collimator lens 307. The reference light LR is dimmed by a neutral density (ND) filter 308, and reflected in the opposite direction by a corner cube 309. Then, an image is formed on the reflection surface of a reference mirror 311 by a collimator lens 310. The reference system unit including the corner cube 309 is integrally movable along the traveling direction of the reference light LR. The correction according to the axial length of the eye E can be performed by moving the reference system unit. The reference light LR reflected on the reference mirror 311 travels through the same path in the opposite direction, and is guided to the fiber coupler 303. Incidentally, an optical element for dispersion compensation (pair prism, etc.), an optical element for polarization compensation (wave plate, etc.), and the like may be provided on the optical path (reference light path) of the reference light LR.

The fiber coupler 303 superposes the return light of the measuring light LS on the reference light LR reflected by the reference mirror 311. The interference light LC thus generated is guided by an optical fiber 312 and emitted from an exit end 313. Besides, the interference light LC is collimated into a parallel light beam by a collimator lens 314, and dispersed (resolved into spectra) by a diffraction grating 315. The interference light LC is then condensed by a condenser lens 316 and projected on the light receiving surface of a CCD 317. Although the diffraction grating 315 illustrated in FIG. 9 is a reflection type, a diffraction grating of a transmission type may also be used.

The CCD 317 is, for example, a line sensor, and detects the spectral components of the interference light LC to convert them to electric charges. The CCD 317 accumulates the electric charges to thereby generate a detection signal. The CCD 317 sends the detection signal to the image forming unit 210c.

While, in this embodiment, a Michelson interferometer is employed, any type of interferometers such as, for example, a Mach-Zehnder interferometer, may be used as appropriate. Further, in place of the CCD image sensor, an image sensor of another type such as, for example, a complementary metal oxide semiconductor (CMOS) image sensor, may be used.

Figure 10:
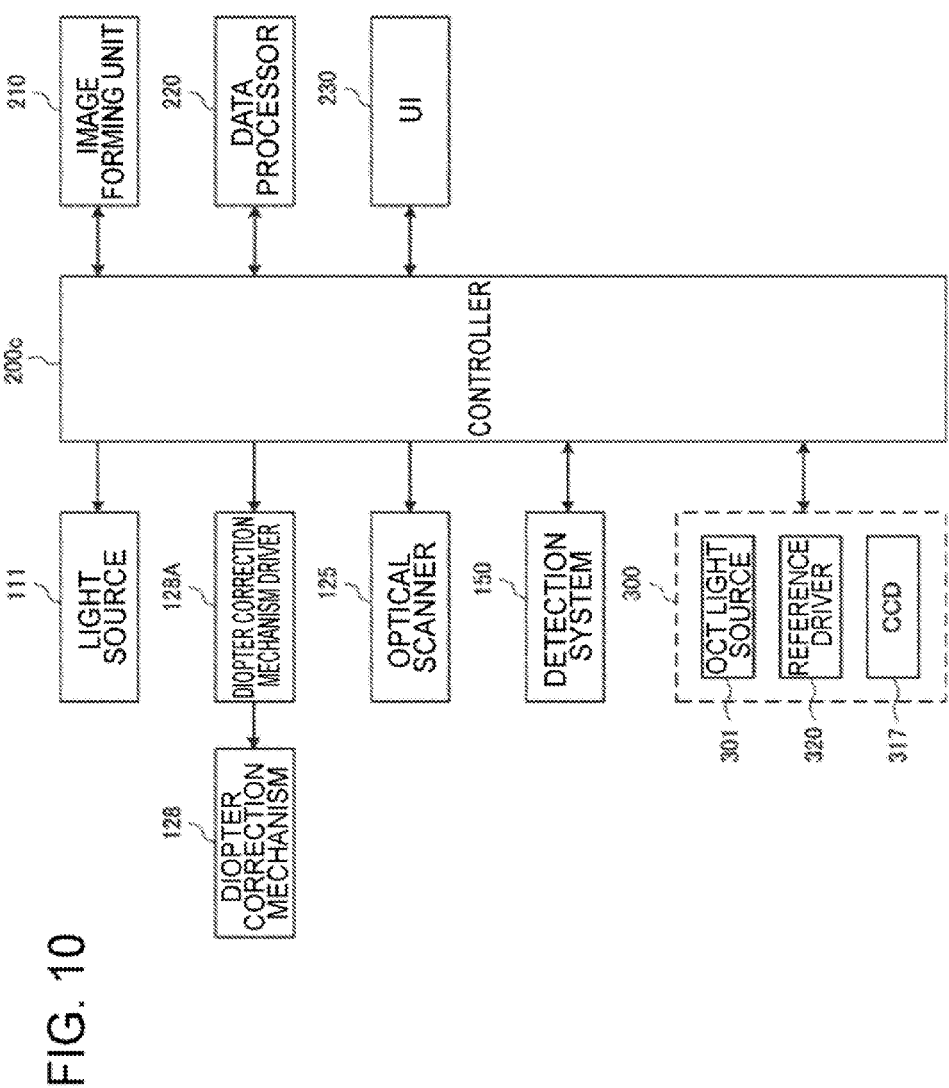
FIG. 10 is a schematic diagram illustrating an example of the configuration of a processing system of the fundus imaging apparatus of the third embodiment.

FIG. 10 illustrates an example of the configuration of a processing system of the fundus imaging apparatus according to the third embodiment. In FIG. 10, like reference numerals designate like parts as in FIGS. 4, 8, and 9. The same description may not be repeated.

In addition to the same control as performed by the controller 200, a controller 200c performs control for the OCT optical system 300 and control for the image forming unit 210c that forms an OCT image. As examples of the control for the OCT optical system 300, the controller 200c controls the OCT light source 301, a reference driver 320, the CCD 317, and the like. Examples of the control for the OCT light source 301 include ON/OFF control of the light source, adjustment of amount of light, adjustment of aperture, and the like. Examples of the control for the reference driver 320 include control for moving the reference system unit along the traveling direction of the reference light LR. Examples of the control for the CCD 317 include adjustment of exposure, adjustment of gain, adjustment of imaging rate, and the like.

The image forming unit 210c is capable of forming an OCT image as well as an SLO image and a phase contrast image described above. The image forming unit 210c forms image data of a cross sectional image of the fundus Ef based on the detection signal received from the CCD 317. Similarly to the conventional Fourier domain optical coherence tomography, the image forming processing includes noise cancellation (noise reduction), filtering, fast Fourier transform (FFT), and the like. The data processor 220 performs known image processing such as interpolation for interpolating pixels between cross sectional images. Thereby, the data processor 220 can form image data of a three-dimensional image of the fundus Ef. The image data of a three-dimensional image refers to image data in which the positions of pixels are defined by a three-dimensional coordinate system. Examples of the image data of a three-dimensional image include image data composed of three-dimensionally arranged voxels. This image data is called volume data or voxel data. When displaying an image based on volume data, the data processor 220 performs rendering (volume rendering, maximum intensity projection (MIP), etc.) on the volume data, thereby forming image data of a pseudo three-dimensional image viewed from a particular line of sight. The pseudo three-dimensional image is displayed on a display device of the user interface 230.

Further, stack data of a plurality of cross sectional images can be formed as the image data of a three-dimensional image. The stack data is image data that can be obtained by arranging a plurality of cross sectional images captured along a plurality of scan lines three-dimensionally based on the positional relationship of the scan lines. That is, the stack data is image data that is obtained by representing a plurality of cross sectional images, each originally defined by their individual two-dimensional coordinate systems, by a single three-dimensional coordinate system (i.e., by embedding the images in one three-dimensional space).

With the fundus imaging apparatus having the configuration described above, the same effects as in the first embodiment can be achieved. Further, an OCT image can be obtained.

Fourth Embodiment

The fundus imaging apparatus of one embodiment may have a configuration according to any combination of the first to third embodiments. In the fourth embodiment, the optical system of the fundus imaging apparatus includes an AO-SLO and an OCT optical system.

The fundus imaging apparatus of the fourth embodiment has basically the same configuration as that of the fundus imaging apparatus of the second embodiment except the presence of the OCT optical system 300 of the third embodiment. In the following, the fundus imaging apparatus of the fourth embodiment is described focusing on differences from the second embodiment and the third embodiment.

Figure 11:
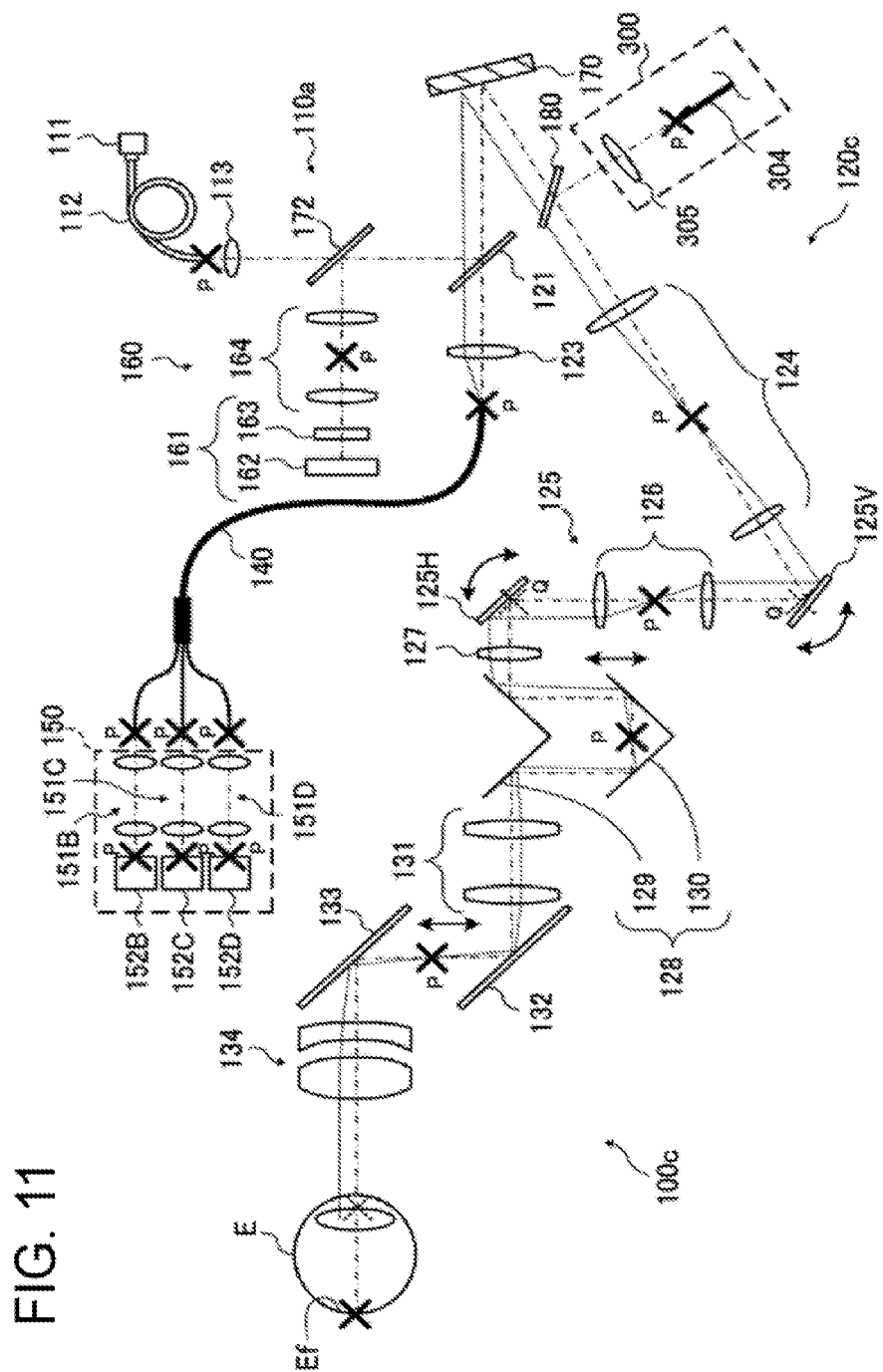
FIG. 11 is a schematic diagram illustrating an example of the configuration of an optical system of a fundus imaging apparatus according to a fourth embodiment.

FIG. 11 illustrates an example of the configuration of the optical system of the fundus imaging apparatus according to the fourth embodiment. In FIG. 11, like reference numerals designate like parts as in FIGS. 6 and 8. The same description may not be repeated.

An optical system 100c of the fourth embodiment is different from the optical system 100a of the second embodiment in that a light guide system 120c is provided in place of the light guide system 120a. In the light guide system 120c, the dichroic mirror 180 is arranged between the deformable mirror 170 and the lens system 124. The dichroic mirror 180 transmits a laser beam emitted from the light source 111, and transmits the fundus reflection light from the fundus Ef of the subject's eye E. Besides, the dichroic mirror 180 reflects the measuring light LS from the OCT optical system 300 toward the optical scanner 125, and also reflects the return light of the measuring light LS returning from the subject's eye E to the OCT optical system 300.

According to the fourth embodiment, in the processing system of the fundus imaging apparatus, the controller performs the control for the OCT optical system 300 performed by a controller 200b illustrated in FIG. 8, in addition to the control performed by the controller 200a illustrated in FIG. 7. Otherwise, the fourth embodiment is the same as the second embodiment and the third embodiment.

With the fundus imaging apparatus having the configuration described above, the same effects as in the first embodiment can be achieved. Further, an SLO image, which is compensated by the adaptive optical system, and an OCT image can be obtained.

While the above embodiments describe examples in which the optical systems are formed of refraction systems, an optical system formed of reflection systems may be used.

In the above embodiments, the detection system 150 is described as including the photodetectors each arranged in one of the exit ends of the multi-branch bundle fiber 140; however, the configuration of the optical system of the fundus imaging apparatus of the embodiments is not so limited. For example, the detection system 150 may have a configuration in which a single photodetector is provided with respect to a plurality of exit ends of the multi-branch bundle fiber 140. In this case, the single photodetector can detect the light output from each of the exit ends by detecting the light output from the exit ends in a time division manner. Alternatively, the detection surface of the single photodetector may be divided to detect the light from each of the exit ends.

In the above embodiments, the multi-branch bundle fiber may be a multi-branch image fiber provided with a plurality of exit ends.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A fundus imaging apparatus, comprising:
   a light source;
   an optical scanner configured to scan a fundus of a subject's eye with light from the light source;
   an optical fiber including a plurality of optical waveguides;
   a light guide system configured to guide the light returning from the fundus to an entrance end of the optical fiber; and
   a photodetector configured to detect light output from each of at least three regions at an exit end of the optical fiber;
   wherein a first image is formed based on a detection result of light output from a first region of the at least three regions, and a second image is formed based on detection results of light output from two or more regions of the at least three regions other than the first region, optical waveguides of the optical fiber in the two or more regions other than the first region being arranged at a position off of an optical axis of a light guide section, and
   wherein an entrance end of at least one of the optical waveguides included in the first region is arranged on an optical axis of the light guide system,
   wherein the first region is a detection area of light in a center area of a point image of a fundus conjugate position,
   wherein the two or more regions other than the first region are a detection area of light around the center area of the point image of the fundus conjugate position,
   wherein the first image is a confocal image and the second image is a non-confocal image.

2. The fundus imaging apparatus of claim 1, wherein:
   a relative position between the entrance end of the optical fiber and the light guide system is changed based on the detection result of the light output from the first region.

3. The fundus imaging apparatus of claim 1, wherein an entrance end side of the optical fiber is controlled to rotate.

4. The fundus imaging apparatus of claim 1, wherein
   the photodetector is further configured to detect light output from each of five or more regions at the exit end, and
   two or more different second images are formed based on detection results of light output from four or more regions of the five or more regions other than the first region.

5. The fundus imaging apparatus of claim 1, wherein the entrance end of the optical fiber is located in a position optically conjugate with the fundus or near the position.

6. The fundus imaging apparatus of claim 1, wherein the photodetector includes three or more photodetectors configured to detect light output from the at least three regions, respectively.

7. The fundus imaging apparatus of claim 1, wherein the first image and the second image are formed simultaneously.

* * * * *

UNITED STATES PATENT AND TRADEMARK OFFICE
CERTIFICATE OF CORRECTION

PATENT NO. : 10,182,721 B2
APPLICATION NO. : 15/202963
DATED : January 22, 2019
INVENTOR(S) : Akemi Miwa et al.

Page 1 of 1

It is certified that error appears in the above-identified patent and that said Letters Patent is hereby corrected as shown below:

On the Title Page

Item (73), the Assignee's city is incorrect. Item (73) should read:
--(73) Assignee: TOPCON CORPORATION, Itabashi-ku (JP)--

Signed and Sealed this
Eighteenth Day of February, 2020

Andrei Iancu
*Director of the United States Patent and Trademark Office*